United States Patent [19]
Reid et al.

[11] Patent Number: 6,017,695
[45] Date of Patent: Jan. 25, 2000

[54] NUCLEIC ACIDS ENCODING HUMAN CELL ADHESION MOLECULE

[75] Inventors: Robert Alan Reid, Durham; John Jacob Hemperly, Apex, both of N.C.

[73] Assignee: Becton Dickinson and Company, Franklin Lakes, N.J.

[21] Appl. No.: 08/040,741

[22] Filed: Mar. 26, 1993

[51] Int. Cl.$^7$ .............................. C12Q 1/68; C07H 21/04
[52] U.S. Cl. ................. 435/6; 435/252.3; 435/320.1; 435/471; 536/23.5; 536/24.31
[58] Field of Search .................. 536/23.5, 24.31, 536/24.33; 530/353, 395; 435/6, 70.1, 172.3, 252.2, 320.1, 810, 471, 252.3; 935/77, 78

[56] References Cited

PUBLICATIONS

Bergund et al Soc Neurosci Abstr., 1992, V18, p. 1325 abstract # 560.5.
Gennarini et al J Cell Biol (Aug. 1989) 109:775–788.
Berglund et al, Eur J. Biochem (1991) 197:549–554.
Brummendorf et al, Neuron (1989) 2:1351–7361.
E. Berglund, et al. "Antigenic Pattern of Human Brain Glycoproteins as Described by Monoclonal Antibodies" *J. Neurochem.* 48:809–815 (1987).
E. Berglund, et al. "Isolation and Characterization of a Membrane Glycoprotein From Human Brain with Sequence Similarities to Cell Adhesion Proteins from Chicken and Mouse" *Eur. J. Biochem.* 197:549–554 (1991).
E. Berglund, et al. "Intracerebral Distribution of Gp135, a New Human Brain Glycoprotein" *Brain. Res.* 549:292–296 (1991).
E. Berglund, et al. "Characterization of cDNAs Encoding Human Contactin" *Soc. Neurosci. Absts.* 18:1325 (1992).
T. Brümmendorf, et al. "Neural Cell Recognition Molecule F11: Homology with Fibronectin Type III and Immunoglobulin Type C Domains" *Neuron* 2:1351–1361 (1989).
G. Gennarini, et al. "The Mouse Neuronal Cell Surface Protein F3: A Phosphatidylinositol–anchored Member of the Immunoglobulin Superfamily Related to Chicken Contactin" *J. Cell Biol.* 109:775–788 (1989).
B. Ranscht, et al. "Sequence of Contactin, a 130–kD Glycoprotein Concentrated in Areas of Interneuronal Contact, Defines a New Member of theh Immunoglobulin Supergene Family in the Nervous System" *J. Cell Biol.* 107:1561–1573 (1988).

*Primary Examiner*—Carla J. Myers
*Attorney, Agent, or Firm*—Donna R. Fugit

[57] ABSTRACT

A human brain glycoprotein homologous to the mouse F3 and the chicken contactin/F11 adhesion molecules, nucleic acid sequences encoding the human brain glycoprotein and antibodies directed against the human brain glycoprotein.

11 Claims, 1 Drawing Sheet

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Mouse (xi) SEQUENCE DESCRIPTION: SEQ ID NO:1:

TAGACCGGAT GGCCAACA                                                  18

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: Mouse (xi) SEQUENCE DESCRIPTION: SEQ ID NO:2:

CTCGACAACA TACTCTCC                                                  18

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Mouse (xi) SEQUENCE DESCRIPTION: SEQ ID NO:3:

CTCTGGTGAT CACAAATC                                                  18

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: Mouse (xi) SEQUENCE DESCRIPTION: SEQ ID NO:4:

TCATCTGAGA GAATCGTC                                                  18

(2) INFORMATION FOR SEQ ID NO:5:

(i) SEQUENCE CHARACTERISTICS:
        (A) LENGTH: 3360 base pairs
        (B) TYPE: nucleic acid
        (C) STRANDEDNESS: both
        (D) TOPOLOGY: linear (ii) MOLECULE TYPE: cDNA (iii) HYPOTHETICAL: NO -continued

```
      (iv) ANTI-SENSE: NO (vi) ORIGINAL SOURCE:
           (A) ORGANISM: Homo sapiens (ix) FEATURE:
           (A) NAME/KEY: CDS
           (B) LOCATION: 122..3175

(ix) FEATURE:
           (A) NAME/KEY: mat_peptide
           (B) LOCATION: 182..3100

(ix) FEATURE:
           (A) NAME/KEY: sig_peptide
           (B) LOCATION: 122..181

(ix) FEATURE:
           (A) NAME/KEY: 5'UTR
           (B) LOCATION: 10..121

(ix) FEATURE:
           (A) NAME/KEY: 3'UTR
           (B) LOCATION: 3176..3360

(ix) FEATURE:
           (A) NAME/KEY: polyA_site
           (B) LOCATION: 3281..3286

(ix) FEATURE:
           (A) NAME/KEY: misc_feature
           (B) LOCATION: 1..9
           (D) OTHER INFORMATION: /function= "EcoRI cloning linker"
               /product= "none"

(ix) FEATURE:
           (A) NAME/KEY: misc_feature
           (B) LOCATION: 3101..3175
           (D) OTHER INFORMATION: /function= "Attachment to
               glycolipid"
               /product= "COOH-signal peptide"

(xi) SEQUENCE DESCRIPTION: SEQ ID NO:5:

GAATTCCGGC TGTGCCGCAC CGAGGCGAGC AGGAGCAGGG AACAGGTGTT TAAAATTATC   60

CAACTGCCAT AGAGCTAAAT TCTTTTTTGG AAAATTGAAC CGAACTTCTA CTGAATACAA  120

G ATG AAA ATG TGG TTG CTG GTC AGT CAT CTT GTG ATA ATA TCT ATT       166
  Met Lys Met Trp Leu Leu Val Ser His Leu Val Ile Ile Ser Ile
  -20              -15                 -10

ACT ACC TGT TTA GCA GAG TTT ACA TGG TAT AGA AGA TAT GGT CAT GGA    214
Thr Thr Cys Leu Ala Glu Phe Thr Trp Tyr Arg Arg Tyr Gly His Gly
 -5              1               5                  10

GTT TCT GAG GAA GAC AAA GGA TTT GGA CCA ATT TTT GAA GAG CAG CCA    262
Val Ser Glu Glu Asp Lys Gly Phe Gly Pro Ile Phe Glu Glu Gln Pro
             15                  20                  25

ATC AAT ACC ATT TAT CCA GAG GAA TCA CTG GAA GGA AAA GTC TCA CTC    310
Ile Asn Thr Ile Tyr Pro Glu Glu Ser Leu Glu Gly Lys Val Ser Leu
         30                  35                  40

AAC TGT AGG GCA CGA GCC AGC CCT TTC CCG GTT TAC AAA TGG AGA ATG    358
Asn Cys Arg Ala Arg Ala Ser Pro Phe Pro Val Tyr Lys Trp Arg Met
     45                  50                  55

AAT AAT GGG GAC GTT GAT CTC ACA AGT GAT CGA TAC AGT ATG GTA GGA    406
Asn Asn Gly Asp Val Asp Leu Thr Ser Asp Arg Tyr Ser Met Val Gly
 60                  65                  70                  75

GGA AAC CTT GTT ATC AAC AAC CCT GAC AAA CAG AAA GAT GCT GGA ATA    454
Gly Asn Leu Val Ile Asn Asn Pro Asp Lys Gln Lys Asp Ala Gly Ile
             80                  85                  90

TAC TAC TGT TTA GCA TCT AAT AAC TAC GGG ATG GTC AGA AGC ACT GAA    502
Tyr Tyr Cys Leu Ala Ser Asn Asn Tyr Gly Met Val Arg Ser Thr Glu
         95                 100                 105
```

-continued

```
GCA ACC CTG AGC TTT GGA TAT CTT GAT CCT TTC CCA CCT GAG GAA CGT      550
Ala Thr Leu Ser Phe Gly Tyr Leu Asp Pro Phe Pro Pro Glu Glu Arg
        110                 115                 120

CCT GAG GTC AGA GTA AAA GAA GGG AAA GGA ATG GTG CTT CTC TGT GAC      598
Pro Glu Val Arg Val Lys Glu Gly Lys Gly Met Val Leu Leu Cys Asp
125                 130                 135

CCC CCA TAC CAT TTT CCA GAT GAT CTT AGC TAT CGC TGG CTT CTA AAT      646
Pro Pro Tyr His Phe Pro Asp Asp Leu Ser Tyr Arg Trp Leu Leu Asn
140                 145                 150                 155

GAA TTT CCT GTA TTT ATC ACA ATG GAT AAA CGG CGA TTT GTG TCT CAG      694
Glu Phe Pro Val Phe Ile Thr Met Asp Lys Arg Arg Phe Val Ser Gln
            160                 165                 170

ACA AAT GGC AAT CTC TAC ATT GCA AAT GTT GAG GCT TCC GAC AAA GGC      742
Thr Asn Gly Asn Leu Tyr Ile Ala Asn Val Glu Ala Ser Asp Lys Gly
                175                 180                 185

AAT TAT TCC TGC TTT GTT TCC AGT CCT TCT ATT ACA AAG AGC GTG TTC      790
Asn Tyr Ser Cys Phe Val Ser Ser Pro Ser Ile Thr Lys Ser Val Phe
            190                 195                 200

AGC AAA TTC ATC CCA CTC ATT CCA ATA CCT GAA CGA ACA ACA AAA CCA      838
Ser Lys Phe Ile Pro Leu Ile Pro Ile Pro Glu Arg Thr Thr Lys Pro
205                 210                 215

TAT CCT GCT GAT ATT GTA GTT CAG TTC AAG GAT GTA TAT GCA TTG ATG      886
Tyr Pro Ala Asp Ile Val Val Gln Phe Lys Asp Val Tyr Ala Leu Met
220                 225                 230                 235

GGC CAA AAT GTG ACC TTA GAA TGT TTT GCA CTT GGA AAT CCT GTT CCG      934
Gly Gln Asn Val Thr Leu Glu Cys Phe Ala Leu Gly Asn Pro Val Pro
                240                 245                 250

GAT ATC CGA TGG CGG AAG GTT CTA GAA CCA ATG CCA AGC ACT GCT GAG      982
Asp Ile Arg Trp Arg Lys Val Leu Glu Pro Met Pro Ser Thr Ala Glu
            255                 260                 265

ATT AGC ACC TCT GGG GCT GTT CTT AAG ATC TTC AAT ATT CAG CTA GAA     1030
Ile Ser Thr Ser Gly Ala Val Leu Lys Ile Phe Asn Ile Gln Leu Glu
        270                 275                 280

GAT GAA GGC ATC TAT GAA TGT GAG GCT GAG AAC ATT AGA GGA AAG GAT     1078
Asp Glu Gly Ile Tyr Glu Cys Glu Ala Glu Asn Ile Arg Gly Lys Asp
285                 290                 295

AAA CAT CAA GCA AGA ATT TAT GTT CAA GCA TTC CCT GAG TGG GTA GAA     1126
Lys His Gln Ala Arg Ile Tyr Val Gln Ala Phe Pro Glu Trp Val Glu
300                 305                 310                 315

CAC ATC AAT GAC ACA GAG GTG GAC ATA GGC AGT GAT CTC TAC TGG CCT     1174
His Ile Asn Asp Thr Glu Val Asp Ile Gly Ser Asp Leu Tyr Trp Pro
            320                 325                 330

TGT GTG GCC ACA GGA AAG CCC ATC CCT ACA ATC CGA TGG TTG AAA AAT     1222
Cys Val Ala Thr Gly Lys Pro Ile Pro Thr Ile Arg Trp Leu Lys Asn
                335                 340                 345

GGA TAT GCG TAT CAT AAA GGG GAA TTA AGA CTG TAT GAT GTG ACT TTT     1270
Gly Tyr Ala Tyr His Lys Gly Glu Leu Arg Leu Tyr Asp Val Thr Phe
            350                 355                 360

GAA AAT GCC GGA ATG TAT CAG TGC ATA GCT GAA AAC ACA TAT GGA GCC     1318
Glu Asn Ala Gly Met Tyr Gln Cys Ile Ala Glu Asn Thr Tyr Gly Ala
365                 370                 375

ATT TAT GCA AAT GCT GAG TTG AAG ATC TTG GCG TTG GCT CCA ACT TTT     1366
Ile Tyr Ala Asn Ala Glu Leu Lys Ile Leu Ala Leu Ala Pro Thr Phe
380                 385                 390                 395

GAA ATG AAT CCT ATG AAG AAA AAG ATC CTG GCT GCT AAA GGT GGA AGG     1414
Glu Met Asn Pro Met Lys Lys Lys Ile Leu Ala Ala Lys Gly Gly Arg
                400                 405                 410

GTG ATA ATT GAA TGC AAA CCT AAA GCT GCA CCG AAA CCA AAG TTT TCA     1462
Val Ile Ile Glu Cys Lys Pro Lys Ala Ala Pro Lys Pro Lys Phe Ser
            415                 420                 425
```

```
TGG AGT AAA GGG ACA GAG TGG CTT GTC AAT AGC AGC AGA ATA CTC ATT         1510
Trp Ser Lys Gly Thr Glu Trp Leu Val Asn Ser Ser Arg Ile Leu Ile
            430                 435                 440

TGG GAA GAT GGT AGC TTG GAA ATC AAC AAC ATT ACA AGG AAT GAT GGA         1558
Trp Glu Asp Gly Ser Leu Glu Ile Asn Asn Ile Thr Arg Asn Asp Gly
        445                 450                 455

GGT ATC TAT ACA TGC TTT GCA GAA AAT AAC AGA GGG AAA GCT AAT AGC         1606
Gly Ile Tyr Thr Cys Phe Ala Glu Asn Asn Arg Gly Lys Ala Asn Ser
460                 465                 470                 475

ACT GGA ACC CTT GTT ATC ACA GAT CCT ACG CGA ATT ATA TTG GCC CCA         1654
Thr Gly Thr Leu Val Ile Thr Asp Pro Thr Arg Ile Ile Leu Ala Pro
                480                 485                 490

ATT AAT GCC GAT ATC ACA GTT GGA GAA AAC GCC ACC ATG CAG TGT GCT         1702
Ile Asn Ala Asp Ile Thr Val Gly Glu Asn Ala Thr Met Gln Cys Ala
            495                 500                 505

GCG TCC TTT GAT CCT GCC TTG GAT CTC ACA TTT GTT TGG TCC TTC AAT         1750
Ala Ser Phe Asp Pro Ala Leu Asp Leu Thr Phe Val Trp Ser Phe Asn
        510                 515                 520

GGC TAT GTG ATC GAT TTT AAC AAA GAG AAT ATT CAC TAC CAG AGG AAT         1798
Gly Tyr Val Ile Asp Phe Asn Lys Glu Asn Ile His Tyr Gln Arg Asn
525                 530                 535

TTT ATG CTG GAT TCC AAT GGG GAA TTA CTA ATC CGA AAT GCG CAG CTG         1846
Phe Met Leu Asp Ser Asn Gly Glu Leu Leu Ile Arg Asn Ala Gln Leu
540                 545                 550                 555

AAA CAT GCT GGA AGA TAC ACA TGC ACT GCC CAG ACA ATT GTG GAC AAT         1894
Lys His Ala Gly Arg Tyr Thr Cys Thr Ala Gln Thr Ile Val Asp Asn
            560                 565                 570

TCT TCA GCT TCA GCT GAC CTT GTA GTG AGA GGC CCT CCA GGC CCT CCA         1942
Ser Ser Ala Ser Ala Asp Leu Val Val Arg Gly Pro Pro Gly Pro Pro
        575                 580                 585

GGT GGT CTG AGA ATA GAA GAC ATT AGA GCC ACT TCT GTG GCA CTT ACT         1990
Gly Gly Leu Arg Ile Glu Asp Ile Arg Ala Thr Ser Val Ala Leu Thr
            590                 595                 600

TGG AGC CGT GGT TCA GAC AAT CAT AGT CCT ATT TCT AAA TAC ACT ATC         2038
Trp Ser Arg Gly Ser Asp Asn His Ser Pro Ile Ser Lys Tyr Thr Ile
605                 610                 615

CAG ACC AAG ACT ATT CTT TCA GAT GAC TGG AAA GAT GCA AAG ACA GAT         2086
Gln Thr Lys Thr Ile Leu Ser Asp Asp Trp Lys Asp Ala Lys Thr Asp
620                 625                 630                 635

CCC CCA ATT ATT GAA GGA AAT ATG GAG GCA GCA AGA GCA GTG GAC TTA         2134
Pro Pro Ile Ile Glu Gly Asn Met Glu Ala Ala Arg Ala Val Asp Leu
            640                 645                 650

ATC CCA TGG ATG GAG TAT GAA TTC CGC GTG GTA GCA ACC AAT ACA CTG         2182
Ile Pro Trp Met Glu Tyr Glu Phe Arg Val Val Ala Thr Asn Thr Leu
        655                 660                 665

GGT AGA GGA GAG CCC AGT ATA CCA TCT AAC AGA ATT AAA ACA GAC GGT         2230
Gly Arg Gly Glu Pro Ser Ile Pro Ser Asn Arg Ile Lys Thr Asp Gly
            670                 675                 680

GCT GCA CCA AAT GTG GCT CCT TCA GAT GTA GGA GGT GGA GGT GGA AGA         2278
Ala Ala Pro Asn Val Ala Pro Ser Asp Val Gly Gly Gly Gly Gly Arg
685                 690                 695

AAC AGA GAG CTG ACC ATA ACA TGG GCG CCT TTG TCA AGA GAA TAC CAC         2326
Asn Arg Glu Leu Thr Ile Thr Trp Ala Pro Leu Ser Arg Glu Tyr His
700                 705                 710                 715

TAT GGC AAC AAT TTT GGT TAC ATA GTG GCA TTT AAG CCA TTT GAT GGA         2374
Tyr Gly Asn Asn Phe Gly Tyr Ile Val Ala Phe Lys Pro Phe Asp Gly
                720                 725                 730

GAA GAA TGG AAA AAA GTC ACA GTT ACT AAT CCT GAT ACT GGC CGA TAT         2422
Glu Glu Trp Lys Lys Val Thr Val Thr Asn Pro Asp Thr Gly Arg Tyr
            735                 740                 745
```

```
GTC CAT AAA GAT GAA ACC ATG AGC CCT TCC ACT GCA TTT CAA GTT AAA      2470
Val His Lys Asp Glu Thr Met Ser Pro Ser Thr Ala Phe Gln Val Lys
        750                 755                 760

GTC AAG GCC TTC AAC AAC AAA GGA GAT GGA CCT TAC AGC CTA CTA GCA      2518
Val Lys Ala Phe Asn Asn Lys Gly Asp Gly Pro Tyr Ser Leu Leu Ala
765                 770                 775

GTC ATT AAT TCA GCA CAA GAC GCT CCC AGT GAA GCC CCA ACA GAA GTA      2566
Val Ile Asn Ser Ala Gln Asp Ala Pro Ser Glu Ala Pro Thr Glu Val
780                 785                 790                 795

GGT GTA AAA GTC TTA TCA TCT TCT GAG ATA TCT GTT CAT TGG GAA CAT      2614
Gly Val Lys Val Leu Ser Ser Ser Glu Ile Ser Val His Trp Glu His
                800                 805                 810

GTT TTA GAA AAA ATA GTG GAA AGC TAT CAG ATT CGG TAT TGG GCT GCC      2662
Val Leu Glu Lys Ile Val Glu Ser Tyr Gln Ile Arg Tyr Trp Ala Ala
            815                 820                 825

CAT GAC AAA GAA GAA GCT GCA AAC AGA GTT CAA GTC ACC AGC CAA GAG      2710
His Asp Lys Glu Glu Ala Ala Asn Arg Val Gln Val Thr Ser Gln Glu
        830                 835                 840

TAC TCG GCC AGG CTC GAG AAC CTT CTG CCA GAC ACC CAG TAT TTT ATA      2758
Tyr Ser Ala Arg Leu Glu Asn Leu Leu Pro Asp Thr Gln Tyr Phe Ile
    845                 850                 855

GAA GTC GGG GCC TGC AAT AGT GCA GGG TGT GGA CCT CCA AGT GAC ATG      2806
Glu Val Gly Ala Cys Asn Ser Ala Gly Cys Gly Pro Pro Ser Asp Met
860                 865                 870                 875

ATT GAG GCT TTC ACC AAG AAA GCA CCT CCT AGC CAG CCT CCA AGG ATC      2854
Ile Glu Ala Phe Thr Lys Lys Ala Pro Pro Ser Gln Pro Pro Arg Ile
                880                 885                 890

ATC AGT TCA GTA AGG TCT GGT TCA CGC TAT ATA ATC ACC TGG GAT CAT      2902
Ile Ser Ser Val Arg Ser Gly Ser Arg Tyr Ile Ile Thr Trp Asp His
            895                 900                 905

GTC GTT GCA CTA TCA AAT GAA TCT ACA GTG ACG GGA TAT AAG GTA CTC      2950
Val Val Ala Leu Ser Asn Glu Ser Thr Val Thr Gly Tyr Lys Val Leu
        910                 915                 920

TAC AGA CCT GAT GGC CAG CAT GAT GGC AAG CTG TAT TCA ACT CAC AAA      2998
Tyr Arg Pro Asp Gly Gln His Asp Gly Lys Leu Tyr Ser Thr His Lys
    925                 930                 935

CAC TCC ATA GAA GTC CCA ATC CCC AGA GAT GGA GAA TAC GTT GTG GAG      3046
His Ser Ile Glu Val Pro Ile Pro Arg Asp Gly Glu Tyr Val Val Glu
940                 945                 950                 955

GTT CGC GCG CAC AGT GAT GGA GGA GAT GGA GTG GTG TCT CAA GTC AAA      3094
Val Arg Ala His Ser Asp Gly Gly Asp Gly Val Val Ser Gln Val Lys
                960                 965                 970

ATT TCA GGT GCA CCC ACC CTA TCC CCA AGT CTT CTC GGC TTA CTG CTG      3142
Ile Ser Gly Ala Pro Thr Leu Ser Pro Ser Leu Leu Gly Leu Leu Leu
            975                 980                 985

CCT GCC TTT GGC ATC CTT GTC TAC TTG GAA TTC TGAATGTGTT GTGACAGCTG    3195
Pro Ala Phe Gly Ile Leu Val Tyr Leu Glu Phe
        990                 995

CTGTTCCCAT CCCAGCTCAG AAGACACCCT TCAACCCTGG GATGACCACA ATTCCTTCCA    3255

ATTTCTGCGG CTCCATCCTA AGCCAAATAA ATTATACTTT AACAAACTAT TCAACTGATT    3315

TACAACACAC ATGATGACTG AGGCATTCAG GAACCCCTTC ATCCA                    3360

(2) INFORMATION FOR SEQ ID NO:6:

(i) SEQUENCE CHARACTERISTICS:
        (A) LENGTH: 1018 amino acids
        (B) TYPE: amino acid
        (D) TOPOLOGY: linear (ii) MOLECULE TYPE: protein
```

```
(vi) ORIGINAL SOURCE:
     (A) ORGANISM: Homo sapiens (ix) FEATURE:
     (A) NAME/KEY: Disulfide-bond
     (B) LOCATION: 45..94

(ix) FEATURE:
     (A) NAME/KEY: Disulfide-bond
     (B) LOCATION: 138..191

(ix) FEATURE:
     (A) NAME/KEY: Disulfide-bond
     (B) LOCATION: 243..290

(ix) FEATURE:
     (A) NAME/KEY: Disulfide-bond
     (B) LOCATION: 332..371

(ix) FEATURE:
     (A) NAME/KEY: Disulfide-bond
     (B) LOCATION: 416..464

(ix) FEATURE:
     (A) NAME/KEY: Disulfide-bond
     (B) LOCATION: 506..563

(ix) FEATURE:
     (A) NAME/KEY: Domain
     (B) LOCATION: 604..657
     (D) OTHER INFORMATION: /label= FLR
         /note= "conserved core of fibronectin type
         III-like repeat"

(ix) FEATURE:
     (A) NAME/KEY: Domain
     (B) LOCATION: 707..760
     (D) OTHER INFORMATION: /label= FLR
         /note= "conserved core of fibronectin type
         III-like repeat"

(ix) FEATURE:
     (A) NAME/KEY: Domain
     (B) LOCATION: 809..857
     (D) OTHER INFORMATION: /label= FLR
         /note= "conserved core of fibronectin type
         III-like repeat"

(ix) FEATURE:
     (A) NAME/KEY: Domain
     (B) LOCATION: 905..952
     (D) OTHER INFORMATION: /label= FLR
         /note= "conserved core of fibronectin type
         III-like repeat"

(ix) FEATURE:
     (A) NAME/KEY: Modified-site
     (B) LOCATION: 188
     (D) OTHER INFORMATION: /label= ASN-glycos
         /note= "potential site of ASN-linked
         glycosylation"

(ix) FEATURE:
     (A) NAME/KEY: Modified-site
     (B) LOCATION: 238
     (D) OTHER INFORMATION: /label= ASN-glycos
         /note= "potential site of ASN-linked
         glycosylation"

(ix) FEATURE:
     (A) NAME/KEY: Modified-site
     (B) LOCATION: 318
     (D) OTHER INFORMATION: /label= ASN-glycos
         /note= "potential site of ASN-linked
         glycosylation"

(ix) FEATURE:
     (A) NAME/KEY: Modified-site
     (B) LOCATION: 437
```

(D) OTHER INFORMATION: /label= ASN-glycos
                /note= "potential site of ASN-linked
                glycosylation"

(ix) FEATURE:
         (A) NAME/KEY: Modified-site
         (B) LOCATION: 453
         (D) OTHER INFORMATION: /label= ASN-glycos
             /note= "potential site of ASN-linked
             glycosylation"

(ix) FEATURE:
         (A) NAME/KEY: Modified-site
         (B) LOCATION: 474
         (D) OTHER INFORMATION: /label= ASN-glycos
             /note= "potential site of ASN-linked
             glycosylation"

(ix) FEATURE:
         (A) NAME/KEY: Modified-site
         (B) LOCATION: 501
         (D) OTHER INFORMATION: /label= ASN-glycos
             /note= "potential site of ASN-linked
             glycosylation"

(ix) FEATURE:
         (A) NAME/KEY: Modified-site
         (B) LOCATION: 571
         (D) OTHER INFORMATION: /label= ASN-glycos
             /note= "potential site of ASN-linked
             glycosylation"

(ix) FEATURE:
         (A) NAME/KEY: Modified-site
         (B) LOCATION: 913
         (D) OTHER INFORMATION: /label= ASN-glycos
             /note= "potential site of ASN-linked
             glycosylation"

(xi) SEQUENCE DESCRIPTION: SEQ ID NO:6:

Met Lys Met Trp Leu Leu Val Ser His Leu Val Ile Ser Ile Thr
-20              -15                 -10                 -5

Thr Cys Leu Ala Glu Phe Thr Trp Tyr Arg Arg Tyr Gly His Gly Val
                1               5                   10

Ser Glu Glu Asp Lys Gly Phe Gly Pro Ile Phe Glu Glu Gln Pro Ile
            15                  20                  25

Asn Thr Ile Tyr Pro Glu Glu Ser Leu Glu Gly Lys Val Ser Leu Asn
        30                  35                  40

Cys Arg Ala Arg Ala Ser Pro Phe Pro Val Tyr Lys Trp Arg Met Asn
45                      50                  55                  60

Asn Gly Asp Val Asp Leu Thr Ser Asp Arg Tyr Ser Met Val Gly Gly
                65                  70                  75

Asn Leu Val Ile Asn Asn Pro Asp Lys Gln Lys Asp Ala Gly Ile Tyr
            80                  85                  90

Tyr Cys Leu Ala Ser Asn Asn Tyr Gly Met Val Arg Ser Thr Glu Ala
        95                  100                 105

Thr Leu Ser Phe Gly Tyr Leu Asp Pro Phe Pro Glu Glu Arg Pro
    110                 115                 120

Glu Val Arg Val Lys Glu Gly Lys Gly Met Val Leu Leu Cys Asp Pro
125                 130                 135                 140

Pro Tyr His Phe Pro Asp Asp Leu Ser Tyr Arg Trp Leu Leu Asn Glu
                145                 150                 155

Phe Pro Val Phe Ile Thr Met Asp Lys Arg Arg Phe Val Ser Gln Thr
            160                 165                 170

Asn Gly Asn Leu Tyr Ile Ala Asn Val Glu Ala Ser Asp Lys Gly Asn
        175                 180                 185

```
Tyr Ser Cys Phe Val Ser Ser Pro Ser Ile Thr Lys Ser Val Phe Ser
    190                 195                 200

Lys Phe Ile Pro Leu Ile Pro Ile Pro Glu Arg Thr Thr Lys Pro Tyr
205                 210                 215                 220

Pro Ala Asp Ile Val Gln Phe Lys Asp Val Tyr Ala Leu Met Gly
                225                 230                 235

Gln Asn Val Thr Leu Glu Cys Phe Ala Leu Gly Asn Pro Val Pro Asp
            240                 245                 250

Ile Arg Trp Arg Lys Val Leu Glu Pro Met Pro Ser Thr Ala Glu Ile
        255                 260                 265

Ser Thr Ser Gly Ala Val Leu Lys Ile Phe Asn Ile Gln Leu Glu Asp
    270                 275                 280

Glu Gly Ile Tyr Glu Cys Glu Ala Glu Asn Ile Arg Gly Lys Asp Lys
285                 290                 295                 300

His Gln Ala Arg Ile Tyr Val Gln Ala Phe Pro Glu Trp Val Glu His
                305                 310                 315

Ile Asn Asp Thr Glu Val Asp Ile Gly Ser Asp Leu Tyr Trp Pro Cys
            320                 325                 330

Val Ala Thr Gly Lys Pro Ile Pro Thr Ile Arg Trp Leu Lys Asn Gly
        335                 340                 345

Tyr Ala Tyr His Lys Gly Glu Leu Arg Leu Tyr Asp Val Thr Phe Glu
    350                 355                 360

Asn Ala Gly Met Tyr Gln Cys Ile Ala Glu Asn Thr Tyr Gly Ala Ile
365                 370                 375                 380

Tyr Ala Asn Ala Glu Leu Lys Ile Leu Ala Leu Ala Pro Thr Phe Glu
                385                 390                 395

Met Asn Pro Met Lys Lys Ile Leu Ala Ala Lys Gly Gly Arg Val
            400                 405                 410

Ile Ile Glu Cys Lys Pro Lys Ala Ala Pro Lys Pro Lys Phe Ser Trp
        415                 420                 425

Ser Lys Gly Thr Glu Trp Leu Val Asn Ser Ser Arg Ile Leu Ile Trp
    430                 435                 440

Glu Asp Gly Ser Leu Glu Ile Asn Asn Ile Thr Arg Asn Asp Gly Gly
445                 450                 455                 460

Ile Tyr Thr Cys Phe Ala Glu Asn Asn Arg Gly Lys Ala Asn Ser Thr
                465                 470                 475

Gly Thr Leu Val Ile Thr Asp Pro Thr Arg Ile Ile Leu Ala Pro Ile
            480                 485                 490

Asn Ala Asp Ile Thr Val Gly Glu Asn Ala Thr Met Gln Cys Ala Ala
        495                 500                 505

Ser Phe Asp Pro Ala Leu Asp Leu Thr Phe Val Trp Ser Phe Asn Gly
    510                 515                 520

Tyr Val Ile Asp Phe Asn Lys Glu Asn Ile His Tyr Gln Arg Asn Phe
525                 530                 535                 540

Met Leu Asp Ser Asn Gly Glu Leu Leu Ile Arg Asn Ala Gln Leu Lys
                545                 550                 555

His Ala Gly Arg Tyr Thr Cys Thr Ala Gln Thr Ile Val Asp Asn Ser
            560                 565                 570

Ser Ala Ser Ala Asp Leu Val Val Arg Gly Pro Pro Gly Pro Pro Gly
        575                 580                 585

Gly Leu Arg Ile Glu Asp Ile Arg Ala Thr Ser Val Ala Leu Thr Trp
    590                 595                 600

Ser Arg Gly Ser Asp Asn His Ser Pro Ile Ser Lys Tyr Thr Ile Gln
605                 610                 615                 620
```

-continued

```
Thr Lys Thr Ile Leu Ser Asp Asp Trp Lys Asp Ala Lys Thr Asp Pro
            625                 630                 635

Pro Ile Ile Glu Gly Asn Met Glu Ala Ala Arg Ala Val Asp Leu Ile
            640                 645                 650

Pro Trp Met Glu Tyr Glu Phe Arg Val Val Ala Thr Asn Thr Leu Gly
            655                 660                 665

Arg Gly Glu Pro Ser Ile Pro Ser Asn Arg Ile Lys Thr Asp Gly Ala
    670                 675                 680

Ala Pro Asn Val Ala Pro Ser Asp Val Gly Gly Gly Gly Arg Asn
685                 690                 695                 700

Arg Glu Leu Thr Ile Thr Trp Ala Pro Leu Ser Arg Glu Tyr His Tyr
            705                 710                 715

Gly Asn Asn Phe Gly Tyr Ile Val Ala Phe Lys Pro Phe Asp Gly Glu
            720                 725                 730

Glu Trp Lys Lys Val Thr Val Thr Asn Pro Asp Thr Gly Arg Tyr Val
            735                 740                 745

His Lys Asp Glu Thr Met Ser Pro Ser Thr Ala Phe Gln Val Lys Val
    750                 755                 760

Lys Ala Phe Asn Asn Lys Gly Asp Gly Pro Tyr Ser Leu Leu Ala Val
765                 770                 775                 780

Ile Asn Ser Ala Gln Asp Ala Pro Ser Glu Ala Pro Thr Glu Val Gly
            785                 790                 795

Val Lys Val Leu Ser Ser Ser Glu Ile Ser Val His Trp Glu His Val
            800                 805                 810

Leu Glu Lys Ile Val Glu Ser Tyr Gln Ile Arg Tyr Trp Ala Ala His
            815                 820                 825

Asp Lys Glu Glu Ala Ala Asn Arg Val Gln Val Thr Ser Gln Glu Tyr
    830                 835                 840

Ser Ala Arg Leu Glu Asn Leu Leu Pro Asp Thr Gln Tyr Phe Ile Glu
845                 850                 855                 860

Val Gly Ala Cys Asn Ser Ala Gly Cys Gly Pro Pro Ser Asp Met Ile
            865                 870                 875

Glu Ala Phe Thr Lys Lys Ala Pro Pro Ser Gln Pro Pro Arg Ile Ile
            880                 885                 890

Ser Ser Val Arg Ser Gly Ser Arg Tyr Ile Ile Thr Trp Asp His Val
            895                 900                 905

Val Ala Leu Ser Asn Glu Ser Thr Val Thr Gly Tyr Lys Val Leu Tyr
    910                 915                 920

Arg Pro Asp Gly Gln His Asp Gly Lys Leu Tyr Ser Thr His Lys His
925                 930                 935                 940

Ser Ile Glu Val Pro Ile Pro Arg Asp Gly Glu Tyr Val Val Glu Val
            945                 950                 955

Arg Ala His Ser Asp Gly Gly Asp Gly Val Val Ser Gln Val Lys Ile
            960                 965                 970

Ser Gly Ala Pro Thr Leu Ser Pro Ser Leu Leu Gly Leu Leu Leu Pro
    975                 980                 985

Ala Phe Gly Ile Leu Val Tyr Leu Glu Phe
990                 995
```

NUCLEIC ACIDS ENCODING HUMAN CELL ADHESION MOLECULE

FIELD OF THE INVENTION

The present invention relates to cell adhesion molecules and nucleic acid sequences which code for cell adhesion molecules. In particular, the invention pertains to human cell adhesion molecules and nucleic acid sequences which code therefor.

BACKGROUND OF THE INVENTION

Adhesion between cells plays an essential role in development and maintenance of tissue form and function. Intercellular adhesion is mediated by a class of adhesive cell surface proteins commonly referred to as "cell adhesion molecules" or "CAMs". These proteins have been identified and characterized in a phylogenetically diverse range of organisms and have been found in many cases to be highly conserved in structure. Certain cell surface CAMs are members of a superfamily of glycoproteins which are structurally related to immunoglobulins, i.e., their structure contains a number of extracellular immunoglobulin-like and fibronectin Type III-like domains.

The immunoglobulin superfamily of CAMs includes the neural cell adhesion molecule (N-CAM), the L1 antigen, Ng-CAM, TAG-1, and others. These CAMs are believed to mediate homophilic binding between cells and have also recently been recognized as participants in heterophilic interactions with other cell surface molecules, extracellular matrix proteins and proteoglycans. Many are also believed to be involved in transmission of signals to the interior of the cell which modulate cell morphology, cell metabolism and cell adhesion. The means by which these molecules transmit signals to the interior of the cell is unclear.

The F11 antigen (F11) is a chicken neural cell surface-associated glycoprotein which is believed to be involved in neurite-neurite interactions. The cDNA sequence of F11 has been determined and it codes for a 1010 amino acid protein (Bruimmendorf, et al. (1989) Neuron 2:1351–1361). The F11 molecule comprises six domains related to the immunoglobulin domain type C and four domains similar to the fibronectin Type III repeat. These structures are also present in L1 and N-CAM. The cDNA sequence of F11 was found to be almost identical to the cDNA sequence of the chicken neural glycoprotein contactin (Ranscht, et al. (1988) J. Cell Biol. 107:1561–1573; Zisch, et al. (1992) J. Cell Biol. 119:203–213) and it is now believed that the molecules are the same (contactin/F11). However, prior to Applicants' invention, the identity was not clear. A mouse neural cell surface protein, F3, has been identified and is the homologue of the chicken neuronal cell adhesion protein contactin/F11. The cDNA which codes for F3 has been cloned and sequenced, revealing an open reading frame encoding a 1020 amino acid protein having the characteristics of the immunoglobulin superfamily (G. Gennarini, et al. 1989. J. Cell Biol. 109:775–788).

The present invention relates to CAMs involved in human neural cell adhesion. Specifically, the present invention provides the purification and characterization of the human counterpart of the mouse F3 and chicken contactin/F11 proteins, the preparation of monoclonal and polyclonal antibodies to the human contactin and nucleic acid sequences encoding the human contactin. E. Berglund, et al. (1987. J. Neurochem. 48:809–815) have used monoclonal antibodies to characterize glycoproteins in human brain and have reported isolation and characterization of a molecule identified as Gp135 (E. Berglund, et al. 1991. Eur. J. Biochem. 197:549–554; E. Berglund, et al. 1991. Brain Res. 549:292–296). These authors sequenced the amino terminus of the protein and an internal peptide. On the basis of these sequences they identified a similarity to chicken contactin/F11 and mouse F3, however, the reported amino acid sequence of Gp135 is different from that of the human contactin molecule described herein. It was therefore also unclear prior to Applicants' invention whether or not human Gp135 was the direct homolog of F3, contactin/F11. E. Berglund and B. Ranscht later reported the isolation and partial characterization of cDNA clones encoding Gp135 (1992. Soc. Neurosci. Abst. 18:1325, Abst. # 560.5).

SUMMARY OF THE INVENTION

Using monoclonal antibodies, a human brain glycoprotein (human contactin) homologous to the mouse F3 and the chicken contactin/F11 adhesion molecules has been isolated and characterized. A complete coding sequence of the human contactin gene has been determined by sequencing of human neuroblastoma cDNA clones. The gene could potentially encode other, alternatively spliced complete coding regions as well. At the nucleotide level, the human cDNA is 86% homologous to the mouse F3 cDNA. The deduced amino acid sequences are 95% homologous and predict several common structural features, including six immunoglobulin-like and four fibronectin Type III-like domains, as well as multiple sites for Asn-linked glycosylation. The mouse, chicken and human glycoproteins all contain carboxy-terminal hydrophobic segments which may be important for linking the proteins to the cell surface via a phosphatidylinositol anchor.

The human contactin glycoprotein is approximately 135 kD molecular weight and may be purified by immunoaffinity methods using monoclonal antibodies. Partial sequencing of an internal peptide yielded an amino acid sequence identical to that predicted from the cDNA. The cDNA has been expressed in recombinant host microorganisms and the gene product has been shown to be immunoreactive with polyclonal antisera raised against the monoclonal antibody-purified human contactin antigen. Northern blot analyses of the RNAs of various human tissues demonstrated a single major approximately 6.5 kb human contactin transcript in adult brain. Multiple transcripts (6.8 kb, a 6.0 kb doublet and 4.2 kb) are expressed in retinoblastoma and neuroblastoma cell lines. A low level expression of approximately 6.8 and 6.0 kb transcripts, similar to those observed in transformed cell lines, was also detected in human lung and pancreas. Very weak 6.8 and 6.0 kb bands were seen in kidney and skeletal muscle.

DETAILED DESCRIPTION OF THE INVENTION

Figure 1:
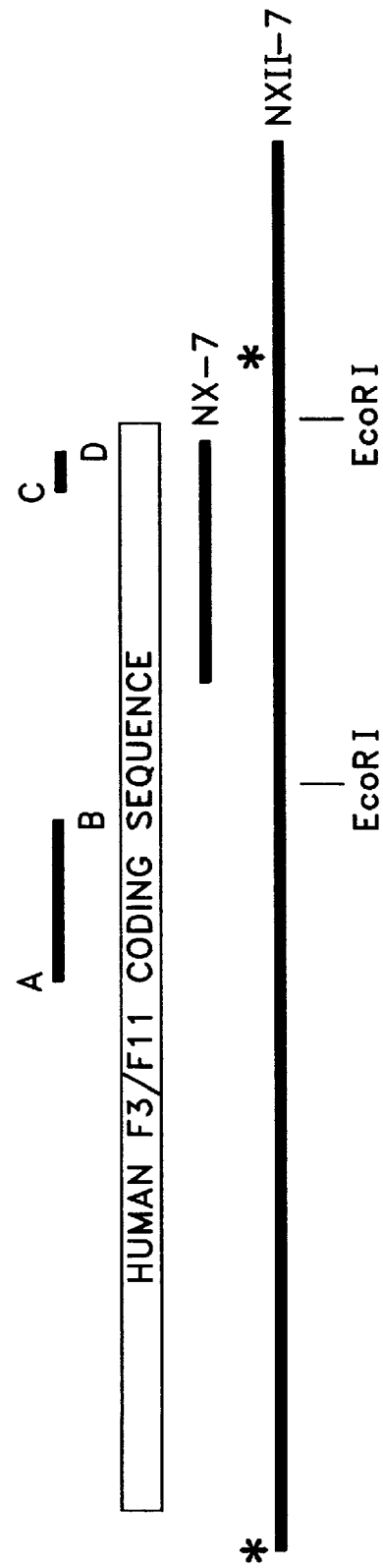
FIG. 1 illustrates the relationships of the mouse F3 probes used to clone the human contactin cDNA, the cDNAs carried in the NX-7 and NXII-7 clones and the human contactin coding sequence.

The human contactin cell adhesion protein of the invention may be isolated from any human neural tissue in which it is expressed. The preferred source is human brain tissue. While conventional chemical and biochemical methods for isolation may be employed, the human contactin cell adhesion protein is most preferably isolated by immunoaffinity methods using antibodies which recognize and bind to it.

Immunoaffinity methods for isolating antigens are well known in the art and may be employed to isolate the human contactin of the present invention using the appropriate monoclonal or polyclonal antibody which recognizes the human contactin molecule. Monoclonal antibodies such as the CF3 antibody described by E. Berglund, et al., supra, or the Neuro-1 antibody described below are preferred, the Neuro-1 antibody being most preferred for isolation of the human contactin protein.

Monoclonal antibodies which recognize the human contactin protein of the invention may be prepared using the methods of Kohler and Milstein ((1975) Nature 256:495) as is known in the art. The preferred antigen for immunization is a preparation of adult human brain membranes and the most preferred antigen is a synaptosomal fraction of these membranes which is enriched for cell surface glycoproteins. Mice may be immunized with the antigen preparation, the spleen cells fused and the resulting hybridomas screened against the original immunogen to select hybridomas.

Using these methods, a hybridoma which produces the monoclonal antibody herein designated Neuro-1 was identified. A crude synaptosomal membrane fraction was prepared from adult human brain tissue (Carlin, R. K., et al. (1980) J. Cell. Biol. 86:831–843)). Membrane glycoproteins were extracted with TERGITOL Type NP-40 (polyglycol ether surfactant, Union Carbide Corp.) and separated by affinity chromatography on immobilized lentil lectin (Pharmacia Biotech, Inc., Piscataway, N.J.) to yield a crude brain glycoprotein fraction. This material was used to immunize C57BL/6 mice (40 µg/mouse). Lymph nodes from animals having the highest serum titers against the immunogen were fused with PcX63Ag8.653 cells (Goding, J. W. (1980) J. Immun. Meth. 39:285–308; ATCC CRL 1580). The resulting hybridomas were screened in enzyme-linked immunosorbent assays (ELISAs) for reactivity with the immunogen and tested for reactivity in immunoblots. A hybridoma secreting an antibody designated Neuro-1 was subcloned by limiting dilution. The Neuro-1 monoclonal antibody was produced in ascites in pristane-primed Balb/C mice and purified by chromatography on Protein A-Sepharose (Sigma Chemical Co., St. Louis, Mo.).

Neuro-1, isotype IgG2b, reacts strongly with the original immunogen in enzyme-linked immunosorbent assays (ELISAs) and recognizes an approximately 135 kD polypeptide on immunoblots. Occasionally, the Neuro-1 antigen appears on immunoblots as a closely spaced doublet. The Neuro-1 producing hybridoma has been deposited with the American Type Culture Collection (Rockville, Md.) on Mar. 3, 1993 under the Accession Number HB11282 and it is the preferred monoclonal antibody for isolation and characterization of the human contactin cell adhesion molecule.

Neuro-1 monoclonal antibody was coupled to Protein A-Sepharose using methyl piperimidate (Harlow, E. and Lane, D. (1988) *Antibodies: A Laboratory Manual*, Cold Spring Harbor Press, p. 522). The membrane extracts described above were then passed over the affinity column and the bound antigen eluted using 0.1 M diethylamine, pH 11.5. The eluted material was concentrated by binding to diethylaminoethyl cellulose (Whatman DE52, Fisher Scientific, Pittsburgh, Pa.) in 0.01 M Tris-HCl and eluted with 1 M NaCl. It was found that if frozen membrane extracts were used in the isolation procedure the Neuro-1 antigen tended to become insoluble. In these cases, the precipitated material was solubilized in deoxycholate, dialyzed against NP40-containing column buffer and processed as above.

Polyclonal antibodies were generated by immunizing animals with the material bound and eluted from immobilized Neuro-1 affinity columns. The polyclonal antibodies were further enriched by chromatography on an immobilized Neuro-1 antigen affinity column.

The 135 kD Neuro-1 antigen was characterized by binding to lentil lectin-Sepharose and elution with glucose, indicating that the polypeptide is glycosylated. The presence of asparagine-linked carbohydrate was verified by treating the antigen with endoglycosidase F (Genzyme, Cambridge, Mass.) and showing a shift to a lower molecular weight. The antigen was found to be released from the cell surface by phosphatidylinositol-specific phospholipase C, indicating that the molecule is anchored to the surface by a lipid linkage. These analyses were performed by washing crude human brain synaptosomal membrane preparations and suspending them in 0.02 M NaOAc, pH 6.0. The enzyme was added and the samples were incubated for 4 hours at 37° C. The membranes were collected by centrifugation and equivalent amounts of membranes and supernatants were analyzed by immunoblotting. Treatment of the reaction mixtures with zinc or with o-phenanthroline showed inhibition and no inhibition of release, respectively. Both polypeptides of the doublet seen on immunoblots were released by phospholipase C treatment, so it is believed that they do not represent anchored and endogenously released forms of the human contactin molecule.

The amino terminal sequence and the sequence of an internal peptide of the Neuro-1 antigen were determined and compared to the published amino acid sequences of mouse F3 and chicken contactin/F11. Amino terminal sequences were determined using immunoaffinity purified material blotted to IMMOBILON-P (Pall Corp., Glen Cove, N.Y.). The amino terminal sequence data were difficult to interpret and contained a large number of unassigned residues. Although many of these ambiguities involved amino acids which are sometimes difficult to detect by sequence analysis, it is also possible that proteolysis of the molecule creates heterogeneity at the amino terminus. Internal peptides were generated by cleavage with endopeptidase lys-c, separated by HPLC and sequenced. The sequence of the internal peptide was clear and was found to be very similar to peptides in F3 and contactin/F11. In addition, because the human peptide was generated by endopeptidase lys-c cleavage, it is most likely flanked by lysine residues. These residues are also conserved in mouse and chicken. On the basis of the amino acid sequence similarities, it is believed that the Neuro-1 antigen is the human counterpart of F3 and contactin/F11. It is therefore referred to herein as human contactin. cDNAs encoding the Neuro-1 antigen were cloned to confirm its identity as human contactin. Mouse F3 probes were used to screen a human neuroblastoma cDNA library (Clontech, Palo Alto, Calif.). The probes were generated by reverse transcriptase-polymerase chain reaction (RT-PCR) of mouse brain polyA+ RNA using primer pairs based on the mouse F3 sequence as reported by Gennarini, et al. supra, (GENBANK locus: musF3, accession #X14943). To perform the RT-PCR, mouse brain polyA+ RNA was prepared using the oligo d(T) cellulose method (Maniatis, et al. *Molecular Cloning—A Laboratory Manual*, Cold Spring Harbor Laboratory. 1982). The RT-PCR amplification reaction was based on the one-step protocol described by Goblet, et al. (1989. Nucleic Acids Res. 17:2144). PolyA+ RNA (1 µg) and 300 ng of each primer (see below) in 66 µl DEPC water were incubated at 65° C. for 15 min. and cooled on ice. Thirty-three µl of 3×RT-PCR reagent mix (3×X PCR buffer, 150 mM KCl, 30 mM Tris-Cl pH 8.3, 4.5 mM $MgCl_2$, 0.3% gelatin, 500 µM dNTPs, 200 U M-MLV reverse transcriptase, 4 U rRNAsin (Promega, Madison, Wis.), 2.5 U AMPLITAQ (Perkin-Elmer Cetus, Norwalk, Conn.) was added and the reaction was incubated at 37° C. for 30 min., followed by 94° C. for 1 min, 50° C for 2 min., and 72° C. for 2 min. The amplification reaction was repeated for 40 cycles. Primer pairs A/B and C/D were used for amplification of the mouse F3 probes:

| PRIMER FIG. 1 | SEQUENCE ID NO. | SEQUENCE* | NUCLEOTIDE POSITION IN musF3 |
|---|---|---|---|
| A | SEQ ID NO:3 | CTCTGGTGATCACAAATC | 1742–1759 |
| B | SEQ ID NO:4 | TCATCTGAGAGAATCGTC | 2181–2198 |
| C | SEQ ID NO:1 | TAGACCGGATGGCCAACA | 3087–3104 |
| D | SEQ ID NO:2 | CTCGACAACATACTCTCC | 3163–3180 |

*Primers B and D are inverse complements of musF3.

The probes were verified as mouse F3 by direct sequencing with SEQUENASE (United States Biochemical Corp., Cleveland, Ohio) performed as described by Mihovilovic ((1989) BioTechniques 7:14–16). This is an efficient method for sequencing PCR amplified DNA. The PCR products of primer pair SEQ ID NO:1/SEQ ID NO:2 (94 bp) and SEQ ID NO:3/SEQ ID NO:4 (457 bp) were gel purified and re-amplified using asymmetric primer concentrations to produce the single-stranded sequencing templates.

Using the mouse SEQ ID NO:1/SEQ ID NO:2 probe prepared above, a human Kelly neuroblastoma lambda gt10 cDNA library (Clontech, Palo Alto, Calif.) was screened as recommended by the manufacturer. Two cDNA clones were isolated, including the clone NX-7 which contained the cDNA shown in FIG. 1. To obtain clones containing upstream sequences, the neuroblastoma library was screened using the mouse SEQ ID NO:3/SEQ ID NO:4 probe. Three clones were identified from this screening, including one which was a full-length clone containing the entire coding sequence. This clone was designated clone NXII-7. Lambda cDNA inserts were either PCR amplified using lambda gt10 EcoRI forward and reverse primers and sequenced directly or subcloned into pBLUESCRIPT (SK+) (Stratagene, La Jolla, Calif.) prior to sequencing. The pBLUESCRIPT subclones were sequenced manually by either dideoxy termination with SEQUENASE or by dye-termination or dye-labeled primer automated sequencing (Applied Biosystems, Model 373A, Foster City, Calif.) as recommended by the manufacturers. Sequencing primers were synthesized on an Applied Biosystems (ABI) Model 380B DNA synthesizer and purified using OPC cartridges (ABI) as recommended. Sequence alignments, translations, and features location were performed using IG-Suite software (Intelligenetics, Mountain View, Calif.). The cDNAs produced by this procedure may be used as probes to isolate the genomic DNA coding for human contactin.

The entire human contactin cDNA coding and partial 5' and 3' untranslated sequence was determined by sequencing both strands of cDNAs (SEQ ID NO:5; EMBL Accession #21488). Among the various cDNA clones, two single base variations were observed at positions 2424 and 2513. These result in valine to alanine and leucine to valine transitions, respectively. Human contactin cDNA contains a 3054 bp open reading frame which is capable of encoding a polypeptide 1018 amino acids in length (SEQ ID NO:6). The predicted polypeptide contains hydrophobic segments at the amino-terminal and carboxyl-terminal ends. The amino terminal hydrophobic segment contains a consensus processing site and is believed to be a signal sequence which is cleaved to yield the amino terminus of the mature polypeptide. The hydrophobic segment at the carboxyl terminus is similar to segments found at the carboxyl ends of other phosphatidylinositol-linked membrane proteins and it is believed to be removed during the attachment to glycolipid. The fact that the Neuro-1 antigen is released from the cell surface by phosphatidylinositol-specific phospholipase C is consistent with this hypothesis. Included in the predicted amino acid sequence of the polypeptide, at positions 836–850, is the sequence of the Neuro-1 antigen lys-c peptide described above, confirming that the Neuro-1 antigen is the human contactin cell adhesion molecule.

As previously disclosed, Berglund, et al. have reported a molecule designated Gp135 which they describe as a possible human homologue of mouse F3 and chicken contactin/F11. However, the Berglund, et al. internal peptide sequence is only 71% similar to the deduced amino acid sequence of a corresponding peptide (residues 679–693) of the present invention.

The deduced amino acid sequence of human contactin contains six immunoglobulin-like domains followed by four fibronectin Type III-like repeats. This structure is similar to mouse F3 and chicken contactin/F11. In the second fibronectin Type III repeat the carboxyl-terminal conserved tyrosine is replaced by phenylalanine as in mouse F3. There are nine consensus sites for asparagine-linked glycosylation, all of which are conserved between human and mouse. The deduced human and mouse polypeptide sequences are 95% homologous and differ in size by two amino acids. Mouse F3 contains a single dipeptide insert within the sixth immunoglobulin-like domain which is absent in human contactin and chicken contactin/F11. It is not known whether this sequence gap is the result of alternate RNA splicing or a reflection of intra-exonic differences between species. The regions of lowest sequence identity have about 70% homology and are located in the hydrophobic amino terminal and carboxyl-terminal segments.

Polyclonal antisera were generated in rabbits using immunoaffinity purified human contactin to further confirm that the Neuro-1 antigen is the human homologue of F3 and contactin/F11. The sera recognized the immunogen in immunoblots at a 1:12,000 dilution. The sera also reacted with a glutathione S-transferase/human contactin fusion protein expressed in bacteria. The human contactin portion of this fusion protein comprised the carboxy-terminal region of human contactin, corresponding to the cDNA in clone NX-7, cloned in pGEX-2T (Pharmacia, Piscataway, N.J.).

The upstream EcoRI fragment of the cDNA insert of NMI-7 and the entire cDNA insert of NX-7 were used as probes to characterize the expression pattern of human contactin in various tissues. Human brain contained a single major approximately 6.5 kb mRNA. This transcript is larger than is necessary to encode the human contactin protein and is believed to include a large 3' untranslated region which is not completely represented in the cDNA clones isolated. The isolated cDNAs extended no more than about 1.2 kb past the carboxyl-terminus of the human contactin molecule.

Of the other tissues tested, pancreas and lung exhibited a low level of expression (compared to brain) of the 6.8 kb transcript and a 6.0 kb doublet similar to the pattern seen in cell lines (see below). Skeletal muscle and kidney showed similar, yet very weak 6.8 and 6.0 kb transcripts. Heart and liver were negative for human contactin transcripts. The human neuroblastoma cell lines IMR-32, SK-N-MC, SMS-KAN and SK-N-SH contained human contactin mRNA, as did the retinoblastoma cell line Y79. In these cell lines, in contrast to the transcript pattern in brain, multiple RNA species were observed—a 6.8 kb species, a 6.0 kb doublet and a 4.2 kb species. It is unclear in all cases whether or not the approximately 6.8 kb and 6.5 kb transcripts are significantly different. Rhabdomyosarcoma (A204, RD and A673), hematopoietic (KG1a.5), small cell lung carcinoma (SHP77) and Ewing Sarcoma (RD-ES) cell lines did not express human contactin RNA.

The antibodies which recognize human contactin and the nucleotide probes derived from the nucleotide sequence which codes for human contactin are useful in methods for detecting the protein and nucleotide sequences, respectively. Nucleotide probes may comprise the complete cloned cDNA sequence or a portion thereof One skilled in the art will further recognize that nucleotide probes may be designed which comprise all or a portion of a sequence which is complementary to the cloned sequences. To detect the contactin protein, immunoassay methods involving binding between a protein and its antibody such as ELISAs and immunoblots can be readily adapted to employ the antibodies and contactin glycoprotein disclosed herein. These immunoassay methods are known in the art. In general, detection of binding between protein and antibody is accomplished by including a signal moiety in the binding reaction. This is usually in the form of a detectable label conjugated to the antibody or protein. The detectable label may be directly detectable (e.g., a dye, radioisotope or fluorochrome) or rendered detectable after further chemical reaction (e.g., an enzyme which reacts to produce a colored product or biotin which may be bound to labeled avidin).

Detection of nucleic acids by hybridization to a probe is also known in the art. Such methods as Southern blotting, dot blotting and the like may be readily adapted to detection of oligonucleotides containing all or part of a nucleic acid sequence encoding human contactin using the nucleotide sequence information of SEQ ID NO:5 to design appropriate probes. For purposes of the present invention, the terms "encoding" and "coding for" are intended to include nucleic acids which comprise sequences which can be transcribed and/or translated to produce human contactin. That is, both DNA and the RNA transcribed from it are considered to "code for" or "encode" human contactin. It will also be understood that probes derived from the disclosed nucleotide sequences may also be used to detect fragments of the disclosed coding sequences. As for immunoassays, hybridization of the probe to the contactin nucleotide sequence will be detected by means of a directly or indirectly detectable label associated with the probe, i.e., incorporated in the probe or conjugated to it. In general the same labels useful for labeling antibodies and antigens may be used to label oligonucleotides. In addition, it is within the ordinary skill in the art, given the nucleotide sequence of SEQ ID NO:5, to derive the complementary nucleotide sequence, which may also be used to prepare probes and which may be detected by hybridization to probes. Further, the present disclosure of SEQ ID NO:5 as a DNA sequence easily allows derivation of RNA sequences which are complementary to either SEQ ID NO:5 or its complementary strand. Such equivalent RNA sequences may be detected by hybridization to probes as well.

The reagents for performing these immunoassays and hybridization assays may be conveniently packaged together for sale or use in the form of a kit. A kit for immunoassay may contain an antibody which recognizes and binds to human contactin conjugated to a selected label and optionally any reagents necessary for performing the assay and detecting the label. A kit for a hybridization assay may contain short oligonucleotide probes which hybridize to one or more nucleotide sequences contained in SEQ ID NO:5, the probes being conjugated to the selected label. Optionally, the hybridization assay kit may contain any reagents necessary for performing the hybridization assay and detecting the label.

The foregoing disclosure is intended to illustrate the invention but is not to be construed as limiting its scope as defined by the appended claims. Upon reading the present disclosure, certain equivalents and variations will be apparent to one skilled in the art without the exercise of inventive skill and without departing from the spirit of the invention. Such equivalents and variations are intended to be included within its scope.

What is claimed is:

1. A isolated polynucleotide consisting of the nucleotide sequence of SEQ ID NO:5.

2. A isolated polynucleotide having a nucleotide sequence consisting of nucleotides 122–3175 of SEQ ID NO:5.

3. A isolated polynucleotide having a nucleotide sequence consisting of nucleotides 182–3094 of SEQ ID NO:5.

4. A recombinant expression vector comprising the polynucleotides of claims 1, 2 or 3.

5. A host microorganism transformed with the expression vector of claim 4.

6. A method for detecting, in a sample, a nucleotide sequence coding for human contactin comprising contacting the sample under conditions suitable for nucleic acid hybridization with a probe consisting of the nucleotide sequence of SEQ ID NO:5 or the nucleotide sequence of the complementary strand of SEQ ID NO:5, and detecting hybridization of the probe to the nucleotide sequence coding for human contactin.

7. The method of claim 6 wherein hybridization is detected by means of a detectable label associated with the probe.

8. The method of claim 6 wherein a DNA sequence is detected.

9. The method of claim 6 wherein an RNA sequence is detected.

10. A kit of materials for detecting, in a sample, a nucleotide sequence coding for human contactin, the kit comprising, an enclosure, a probe consisting of the nucleotide sequence of SEQ ID NO:5 or its complementary strand and means for detecting hybridization of the probe to the oligonucleotide.

11. The kit of claim 10 wherein the means for detecting hybridization comprises a detectable label conjugated to the probe.

\* \* \* \* \*